United States Patent
Takizawa et al.

(10) Patent No.: US 8,426,455 B2
(45) Date of Patent: Apr. 23, 2013

(54) PROPHYLACTIC AND/OR THERAPEUTIC AGENT FOR HYPERLIPIDEMIA

(75) Inventors: Toshiaki Takizawa, Tokyo (JP); Noriyuki Inoue, Tokyo (JP); Katsutoshi Miyosawa, Tokyo (JP)

(73) Assignee: Kowa Company, Ltd., Nagoya-shi (JP)

( * ) Notice: Subject to any disclaimer, the term of this patent is extended or adjusted under 35 U.S.C. 154(b) by 436 days.

(21) Appl. No.: 12/593,356

(22) PCT Filed: Mar. 28, 2008

(86) PCT No.: PCT/JP2008/000788
§ 371 (c)(1),
(2), (4) Date: Sep. 28, 2009

(87) PCT Pub. No.: WO2008/120472
PCT Pub. Date: Oct. 9, 2008

(65) Prior Publication Data
US 2010/0069433 A1 Mar. 18, 2010

(30) Foreign Application Priority Data
Mar. 29, 2007 (JP) .................. 2007-087081

(51) Int. Cl.
*A61K 31/42* (2006.01)
(52) U.S. Cl.
USPC ............ 514/375; 514/377; 514/188; 548/222
(58) Field of Classification Search .................. 514/375, 514/377, 188; 548/222
See application file for complete search history.

(56) References Cited

U.S. PATENT DOCUMENTS

| | | | |
|---|---|---|---|
| 7,790,903 B2 * | 9/2010 | Yamazaki et al. | 548/222 |
| 2005/0101636 A1 | 5/2005 | Yamazaki et al. | |
| 2006/0189667 A1 | 8/2006 | Yamazaki et al. | |

FOREIGN PATENT DOCUMENTS

| | | |
|---|---|---|
| DE | 10200138 A1 | 7/2003 |
| EP | 1661890 A1 | 5/2006 |
| WO | 00/61556 A1 | 10/2000 |
| WO | 03/013608 A1 | 2/2003 |
| WO | 03/088962 A1 | 10/2003 |
| WO | 2005-023777 A1 | 3/2005 |
| WO | 2005/074909 A1 | 8/2005 |
| WO | 2006/090756 A1 | 8/2006 |
| WO | WO2006/090768 * | 8/2006 |
| WO | 2006/129859 A2 | 12/2006 |

OTHER PUBLICATIONS

Notification of Transmittal of Translation of the International Preliminary Report on Patentability (form PCT/IB/338) of International Application No. PCT/JP2008/000788 mailed Oct. 29, 2009 with Forms PCT/IB/373 and PCT/ISA/237.
T. Teramoto, "Koshiketsusho Chiryo ni Okeru Fibrate-kei Yakuzai no Ichizuke—Daikibo Rinsho Shiken o Furikaette", Therapeutic Research, 2006, p. 1979-1986, 27(10), cited in ISR.
I. Inoue et al., "Fibrate and Statin Synergystically Increase the Transcriptional Activities of PPARa/RXRa and Decrease the Transactivation of NFkB", Biochemical and Biophysical Research Communications, 2002, p. 131-139, No. 290, cited in ISR.
H. Yamazaki et al., "Shinki HMG-CoA Kangen Koso Sogaiyaku Pitavastatin (Livalo-joO) no Yakuri Oyobi Yakubutsu Dotaiteki Tokucho to Rinsho Koka", Folia Pharmacologica Japonica, 2004, p. 349-362, No. 123, cited in ISR.
T. Tanaka et al., "Koshiketsusho Gappei 2-gata Tonyobyo Kanja ni Taisuru Fenofibrate no Chokiteki Yuyosei", Progress in Medicine, 2006, p. 1111-1116, No. 26, cited in ISR.
T. E. Johnson et al., "Statins and PPARa agonists include myotoxicity in differentiated rat skeletal muscle cultures but do not exhibit synergy with co-treatment", Toxicology and Applied Pharmacology, 2005, p. 210-221, No. 208 cited in ISR.
International Search Report for PCT/JP2008/000788, Mailing Date of May 1, 2008.
Supplementary European Search Report dated Apr. 20, 2010, issued in corresponding European Patent Application No. 08720655.3.
Fisman, Enrique et al.; "Statins research unfinished saga: desirability versus feasibility"; Cardiovascular Diabetology 2005, vol. 4, No. 1, 2005, pp. 1-8.
Han, Jihong et al.; "Pitavastation Downregulates Expression of the Macrophage Type B Scavenger Receptor, CD36" Circulation 17, vol. 109, No. 6 , Feb. 17, 2004, pp. 790-796.

(Continued)

*Primary Examiner* — Renee Claytor
*Assistant Examiner* — Shobha Kantamneni
(74) *Attorney, Agent, or Firm* — Westerman, Hattori, Daniels & Adrian, LLP

(57) ABSTRACT

The present invention provides a therapeutic agent for hyperlipidemia having an excellent effect of lowering the cholesterol and triglyceride level in blood plasma.
The present invention relates to a prophylactic and/or therapeutic agent for hyperlipidemia, a prophylactic and/or therapeutic agent for obesity or diabetes mellitus, and a prophylactic and/or therapeutic agent for metabolic syndrome, each agent including a compound represented by the formula (1), or a salt thereof, and a statin, particularly pitavastatin, in combination.

formula (1):

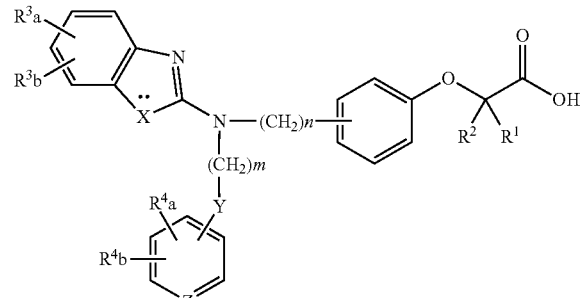

(1)

4 Claims, 2 Drawing Sheets

OTHER PUBLICATIONS

Kleemann, Robert et al. "Evidence for anti-inflammatory activity of statins and PPAR activators in human C-reactive protein transgenic mice in vivo and in cultured human hepatocytes in vitro"; Blood, Jun. 1, 2004, vol. 103, No. 11, pp. 4188-4194.

Saito, Yasushi et al.; "A randomized double-blind trial comparing the efficacy and safety of pitavastatin versus pravastatin in patients with primary hypercholesterolemia"; Atherosclerosis, vol. 162, Jan. 1, 2002, pp. 373-379.

* cited by examiner

PROPHYLACTIC AND/OR THERAPEUTIC AGENT FOR HYPERLIPIDEMIA

TECHNICAL FIELD

The present invention relates to a prophylactic and/or therapeutic agent for hyperlipidemia, particularly to a prophylactic and/or therapeutic agent for hyperlipidemia, exhibiting an excellent lowering effect on any of the cholesterol concentration in blood plasma and the triglyceride concentration in blood plasma. The present invention also relates to a prophylactic and/or therapeutic agent for obesity or diabetes mellitus, and a prophylactic and/or therapeutic agent for metabolic syndrome.

BACKGROUND ART

Hyperlipidemia is a symptom associated with an abnormal increase in the lipoprotein lipids in blood plasma, and since this symptom is strongly associated with diseases such as arteriosclerosis and myocardial infarction, treatment of the symptom has been considered to be important.

For the treatment of hyperlipidemia, various medicaments such as 3-hydroxy-3-methylglutaryl coenzyme A (HMG-CoA) reductase inhibitors (hereinafter, may also be referred to as statin), fibrate-based drugs, nicotinic acid, anion-exchange resins, cholesterol absorption inhibitory drugs, probucol, dextran sulfate and ethyl icosapentate have been used, and statins such as pravastatin, simvastatin, fluvastatin, atorvastatin, pitavastatin and rosuvastatin have taken the leading position in recent therapeutic agents of hyperlipidemia Among the statins, pitavastatin or salts thereof are known to have a potent HMG-CoA reductase inhibitory effect, thus being useful as an agent for lowering the plasma cholesterol concentration (see, Patent Reference 1). However, according to the results of clinical trials, the rate of improvement in the total plasma cholesterol concentration achieved by pravastatin, which is a first generation statin, is 68.6%, while the rate of improvement in the total plasma cholesterol concentration achieved by pitavastatin, which exhibits a strong cholesterol lowering effect, is still the same 93.9%; thus, sufficient improvement in the total cholesterol concentration in blood plasma has not observed in the remaining patients (see, Non-Patent Reference 1).

Yu et al. compared the differences in the effect of drugs in a group of familial hyperlipidemic patients exhibiting resistance to the treatment with a statin, a group of familial hyperlipidemic patients benefiting from the treatment with the same drug, and a group of non-familial hyperlipidemic patients (control group), by utilizing fibroblast cells that have similar properties to hepatic cells. As a result, in the group of familial hyperlipidemic patients benefiting from the treatment with a statin and in the control group, when the cells were brought under the effect of statin, there was an increase in the expression of LDL receptors which have a function of taking up LDL cholesterol from the blood into the liver, along with an increase in the expression of HMG-CoA reductase. On the other hand, in the group of patients exhibiting resistance to the treatment with a statin, the expression of HMG-CoA reductase was increased, but the expression of LDL receptors was not increased. That is, it is proved that one of the mechanisms for the manifestation of resistance to the treatment with a statin is related to the lack of increase in the expression of LDL receptors (see, Non-Patent Reference 2).

It has been reported that a phenomenon similar to the case of the familial hyperlipidemic patients exhibiting resistance to the treatment with a statin, is also observed in rats. In other words, it is a well known fact to those having ordinary skill in the art that statins do not lower the total plasma cholesterol concentration in rats, and the mechanism of such phenomenon has been reported to be based on the observations that (1) even though statins are administered, HMG-CoA reductase is vicariously increased in the liver to maintain cholesterol synthesis, and that (2) in rats, even though statins are administered, LDL receptors are not increased (see, Non-Patent References 3 and 4). Therefore, it is considered that a drug exhibiting an effect of lowering the total plasma cholesterol concentration and the LDL cholesterol level in rat, is also effective in those patients originally exhibiting resistance to the treatment using statins.

Meanwhile, the main components of the lipoprotein lipids in plasma include cholesterol, triglycerides and the like. Since hyperlipidemic patients in many cases have been observed not only to have an increase in the plasma cholesterol concentration, but also to have an increase in the plasma triglyceride concentration, a drug which lowers the plasma triglyceride concentration as well as the plasma cholesterol concentration has been desired. Generally, when statins are administered to hyperlipidemic patients, the plasma cholesterol concentration is sufficiently lowered, but the lowering effect is often insufficient for the plasma triglyceride concentration. However, a method of treating a hyperlipidemic patient having both high plasma cholesterol concentration and high plasma triglyceride concentration, by increasing the dosage of statin for the purpose of lowering both concentrations, has problems in the aspects of safety and the like, and thus has not been recommended.

As the drug for lowering the plasma triglyceride concentration, fibrate-based drugs represented by a fenofibrate are known, and combined use of a statin and a fibrate-based drug has been reported (see, Patent Reference 2, Non-Patent Reference 5). However, combined use of a fibrate-based drug and a statin has been reported to induce the onset of rhabdomyolysis as a side effect, in patients suffering from renal disorders, and thus this combination has been subject to cautious administration.

As another group of drugs for lowering the plasma triglyceride concentration, those created as a result of paying attention to the action of peroxisome proliferators-activated receptor (PPAR) α-activation, which is the operating mechanism for fibrate-based drugs, are known. For example, a phenoxybutyric acid derivative represented by the following formula (1) has been reported to have an effect of lowering the plasma triglyceride concentration, and the derivative is known to be useful for hyperlipidemia, arteriosclerosis, diabetes mellitus, diabetic complications, inflammations, cardiac diseases and the like (see, Patent Reference 3, Non-Patent Reference 6). However, it has not been known of what influence a combination of this phenoxybutyric acid derivative and a statin would exert on the lipids in blood.

Furthermore, diabetes mellitus is a disease having a risk of inducing various characteristic complications, including the "major vascular complications," that is, ischemic cardiac diseases (angina pectoris, myocardial infarction), cerebral infarction and arteriosclerosis obliterans, as well as diabetic neuropathies, diabetic nephropathy, diabetic retinopathy and the like, as a result of a pathological increase in the blood glucose level caused by abnormal glucose metabolism. As the therapeutic agents for diabetes mellitus, insulin, sulfonylurea drugs (SU drugs), biguanide drugs (BG drugs), α-glucosidase inhibitors (αGI drugs), thiazolidine derivatives (TZD drugs) and the like are known. However, it has not been known of what influence would be exerted by a combination of phenoxybutyric acid derivative and statin, on the blood glucose level.

Furthermore, the metabolic syndrome refers to a state in which resistance to insulin (decrease in the operation of insulin) has been developed because of accumulated visceral fat, and thus risk factors of arteriosclerosis such as abnormal glucose metabolism (abnormal glucose tolerance, diabetes mellitus), abnormal lipid metabolism (hypertriglyceridemia, hypo-HDL-chloesterolemia), and hypertension, converge in one individual. Although each one of the risk factors may be expressed at low degrees, when multiple risk factors are present together, the onset of arteriosclerotic diseases increases synergistically. Thus, the metabolic syndrome has attracted global attention in recent years, as a potent risk factor comparable to high cholesterol level. Various drugs for treating each of the risk factors are being produced, but yet no drug has been approved as a therapeutic agent for metabolic syndrome.

Patent Reference 1: JP-A No. 1-279866
Patent Reference 2: U.S. Pat. No. 6,511,985
Patent Reference 3: WO 2005/023777 pamphlet
Non-Patent Reference 1: J. Olin. Therap. Med., 17, 857-883 (2001)
Non-Patent Reference 2: Atherosclerosis, 124, 103-117 (1996)
Non-Patent Reference 3: J. Lipid. Res., 39, 75-84 (1998)
Non-Patent Reference 4: Biochim. Biophys. Acta, 1254, 7-12 (1995)
Non-Patent Reference 5: Diabetes Care, 25, 1198-1202 (2002)
Non-Patent Reference 6: J. Pharmacol. Sci., 103 suppl. 1, 244P (2007)

DISCLOSURE OF THE INVENTION

Problem to be Solved by the Invention

The present invention is to provide a prophylactic and/or therapeutic agent for hyperlipidemia having excellent effects of lowering the cholesterol concentration and triglyceride concentration in blood plasma. The present invention is also to provide a prophylactic and/or therapeutic agent for obesity or diabetesmellitus, and a prophylactic and/or therapeutic agent for metabolic syndrome.

Means for Solving the Problem

The present inventors have conducted a extensive study to solve the above described problems and finally found that when a statin, particularly pitavastatin, is used in combination with a phenoxybutyric acid derivative or a salt thereof represented by the following formula (1), the combination has an excellent effect of lowering both the cholesterol concentration and triglyceride concentration in blood plasma, and thus is useful for the treatment of hyperlipidemia; thereby completed the present invention. The inventors also found that the medicament is useful as a prophylactic and/or therapeutic agent for obesity or diabetes mellitus, and as a prophylactic and/or therapeutic agent for metabolic syndrome.

Thus, the present invention is to provide a prophylactic and/or therapeutic agent for hyperlipidemia, a prophylactic and/or therapeutic agent for obesity or diabetes mellitus, and a prophylactic and/or therapeutic agent for metabolic syndrome, each including a compound represented by the following formula (1)

(1)

wherein:
$R^1$ and $R^2$, which may be identical or different, each represent a hydrogen atom, a methyl group or an ethyl group; $R^3a$, $R^3b$, $R^4a$ and $R^4b$, which may be identical or different, each represent a hydrogen atom, a halogen atom, a nitro group, a hydroxyl group, a $C_{1-4}$ alkyl group, a trifluoromethyl group, a $C_{1-4}$ alkoxy group, a $C_{1-4}$ alkylcarbonyloxy group, a di-$C_{1-4}$ alkylamino group, a $C_{1-4}$ alkylsulfonyloxy group, a $C_{1-4}$ alkylsulfonyl group, a $C_{1-4}$ alkylsulfinyl group, or a $C_{1-4}$ alkylthio group, or $R^3a$ and $R^3b$, or $R^4a$ and $R^4b$ are joined to represent an alkylenedioxy group; X represents an oxygen atom, a sulfur atom or N—$R^5$ (wherein $R^5$ represents a hydrogen atom, a $C_{1-4}$ alkyl group, a $C_{1-4}$ alkylsulfonyl group, or a $C_{1-4}$ alkyloxycarbonyl group); Y represents an oxygen atom, a S(O)l group (l represents a number from 0 to 2), a carbonyl group, a carbonylamino group, an aminocarbonyl group, a sulfonylamino group, an aminosulfonyl group, or an NH group; Z represents CH or N; n represents a number from 1 to 6; and m represents a number from 2 to 6, or a salt thereof, and a statin in combination.

The present invention is further to be described as follows.

(1) A prophylactic and/or therapeutic agent for hyperlipidemia including the compound represented by the above formula (1) or a salt thereof, and a statin in combination.

(2) The prophylactic and/or therapeutic agent according to (1) above, wherein the compound represented by the formula (1) is (R)-2-[3-[[N-(benzoxazol-2-yl)-N-3-(4-methoxyphenoxy)propyl]aminomethyl]phenoxy]butyric acid or a salt thereof.

(3) The prophylactic and/or therapeutic agent according to (1) or (2) above, wherein the statin is pitavastatin.

(4) The prophylactic and/or therapeutic agent according to any one of (1) to (3) above, wherein the hyperlipidemia is familial hyperlipidemia.

(5) A prophylactic and/or therapeutic agent for diabetes mellitus, including the compound represented by the above formula (1) or a salt thereof, and a statin in combination.

(6) The prophylactic and/or therapeutic agent for diabetes mellitus according to (5) above, wherein the compound represented by formula (1) is (R)-2-[3-[[N-(benzoxazol-2-yl)-N-3-(4-methoxyphenoxy)propyl]aminomethyl]phenoxy]butyric acid or a salt thereof.

(7) The prophylactic and/or therapeutic agent for diabetes mellitus according to (5) or (6) above, wherein the statin is pitavastatin.

(8) A prophylactic and/or therapeutic agent for metabolic syndrome, including the compound represented by the above formula (1) or a salt thereof, and a statin in combination.

(9) The prophylactic and/or therapeutic agent for metabolic syndrome according to (8) above, wherein the compound represented by the above formula (1) is (R)-2-[3-[[N-

(benzoxazol-2-yl)-N-3-(4-methoxyphenoxy)propyl]aminomethyl]phenoxy]butyric acid or a salt thereof.

(10) The prophylactic and/or therapeutic agent for metabolic syndrome according to (8) or (9) above, wherein the statin is pitavastatin.

(11) A pharmaceutical composition for the prevention and/or treatment of hyperlipidemia, including the compound represented by the above formula (1) or a salt thereof, a statin, and a pharmaceutically acceptable carrier.

(12) A pharmaceutical composition for the prevention and/or treatment of hyperlipidemia, including a pharmaceutical composition containing the compound represented by the above formula (1) or a salt, and a pharmaceutically acceptable carrier, and a pharmaceutical composition including a statin and a pharmaceutically acceptable carrier, in combination.

(13) The pharmaceutical composition for the prevention and/or treatment of hyperlipidemia according to (11) or (12) above, wherein the compound represented by the above formula (1) is (R)-2-[3-[[N-(benzoxazol-2-yl)-N-3-(4-methoxyphenoxy)propyl]aminomethyl]phenoxy]butyric acid or a salt thereof.

(14) The pharmaceutical composition for the prevention and/or treatment of hyperlipidemia according to any one of (11) to (13) above, wherein the statin is pitavastatin.

(15) The pharmaceutical composition for the prevention and/or treatment of hyperlipidemia according to any one of (11) to (14) above, wherein the hyperlipidemia is familial hyperlipidemia.

(16) A method for preventing and/or treating hyperlipidemia in a patient, the method including administering to a patient of hyperlipidemia an effective amount of a prophylactic and/or therapeutic agent for hyperlipidemia including the compound represented by the above formula (1) or a salt thereof, and a statin in combination.

(17) The method for preventing and/or treating hyperlipidemia in a patient according to (16) above, wherein the compound represented by the formula (1) is (R)-2-[3-[[N-(benzoxazol-2-yl)-N-3-(4-methoxyphenoxy)propyl]aminomethyl]phenoxy]butyric acid or a salt thereof.

(18) The method for preventing and/or treating hyperlipidemia in a patient according to (16) or (17) above, wherein the statin is pitavastatin.

(19) The method for preventing and/or treating hyperlipidemia in a patient according to any one of (16) to (18) above, wherein the hyperlipidemia is familial hyperlipidemia.

(20) Use of the compound represented by the above formula (1) or a salt thereof, and a statin, for the manufacture of a pharmaceutical composition for preventing and/or treating hyperlipidemia.

(21) The use according to (20) above, wherein the compound represented by the formula (1) is (R)-2-[3-[[N-(benzoxazol-2-yl)-N-3-(4-methoxyphenoxy) propyl]aminomethyl]phenoxy]butyric acid or a salt thereof.

(22) The use according to (20) or (21) above, wherein the statin is pitavastatin.

(23) The use according to any one of (20) to (22) above, wherein the hyperlipidemia is familial hyperlipidemia.

(24) A compound represented by the above formula (1) or a salt thereof, for the prevention and/or treatment of hyperlipidemia, used in combination with a statin.

(25) The compound or salt for the prevention and/or treatment according to (24) above, wherein the compound represented by the formula (1) is (R)-2-[3-[[N-(benzoxazol-2-yl)-N-3-(4-methoxyphenoxy)propyl]aminomethyl]phenoxy]butyric acid or a salt thereof.

(26) The compound or salt for the prevention and/or treatment according to (24) or (25) above, wherein the statin is pitavastatin.

(27) The compound or salt for the prevention and/or treatment according to any one of (24) to (26) above, wherein the hyperlipidemia is familial hyperlipidemia.

(28) A pharmaceutical composition for the prevention and/or treatment of diabetes mellitus, including the compound represented by the above formula (1) or a salt thereof, a statin, and a pharmaceutically acceptable carrier.

(29) A pharmaceutical composition for the prevention and/or treatment of diabetes mellitus, including a pharmaceutical composition containing the compound represented by the above formula (1) or a salt thereof, and a pharmaceutically acceptable carrier, and a pharmaceutical composition containing a statin and a pharmaceutically acceptable carrier, in combination.

(30) The pharmaceutical composition for the prevention and/or treatment of diabetes mellitus according to (28) or (29) above, wherein the compound represented by the formula (1) is (R)-2-[3-[[N-(benzoxazol-2-yl)-N-3-(4-methoxyphenoxy)propyl]aminomethyl]phenoxy]butyric acid or a salt thereof.

(31) The pharmaceutical composition for the prevention and/or treatment of diabetes mellitus according to any one of (28) to (30) above, wherein the statin is pitavastatin.

(32) A method for preventing and/or treating diabetes mellitus in a patient, the method including administering to the patient having diabetes mellitus an effective amount of a prophylactic and/or therapeutic agent for diabetes mellitus including the compound represented by the above formula (1) or a salt thereof, and a statin.

(33) The method for preventing and/or treating diabetes mellitus in a patient according to (32) above, wherein the compound represented by the formula (1) is (R)-2-[3-[[N-(benzoxazol-2-yl)-N-3-(4-methoxyphenoxy)propyl]aminomethyl]phenoxy]butyric acid or a salt thereof.

(34) The method for preventing and/or treating diabetes mellitus in a patient according to (32) or (33) above, wherein the statin is pitavastatin.

(35) Use of the compound represented by the above formula (1) or a salt thereof, and a statin, for the manufacture of a pharmaceutical composition for preventing and/or treating diabetes mellitus.

(36) The use according to (35) above, wherein the compound represented by the formula (1) is (R)-2-[3-[[N-(benzoxazol-2-yl)-N-3-(4-methoxyphenoxy)propyl]aminomethyl]phenoxy]butyric acid or a salt thereof.

(37) The use according to (35) or (36) above, wherein the statin is pitavastatin.

(38) A compound represented by the above formula (1) or a salt thereof for the prevention and/or treatment of diabetes mellitus, used in combination with a statin.

(39) The compound or salt for the prevention and/or treatment according to (38) above, wherein the compound represented by the formula (1) is (R)-2-[3-[[N-(benzoxazol-2-yl)-N-3-(4-methoxyphenoxy)propyl]aminomethyl]phenoxy] butyric acid or a salt thereof.

(40) The compound or salt for the prevention and/or treatment according to (38) or (39) above, wherein the statin is pitavastatin.

(41) A pharmaceutical composition for the prevention and/or treatment of metabolic syndrome, including the compound represented by the above formula (1) or a salt thereof, a statin and a pharmaceutically acceptable carrier.

(42) A pharmaceutical composition for the prevention and/or treatment of metabolic syndrome, including a pharmaceutical composition containing the compound represented by the above formula (1) or a salt thereof, and a pharmaceutically acceptable carrier, and a pharmaceutical composition containing a statin and a pharmaceutically acceptable carrier, in combination.

(43) The pharmaceutical composition for the prevention and/or treatment of metabolic syndrome according to (41) or (42) above, wherein the compound represented by the formula (1) is (R)-2-[3-[[N-(benzoxazol-2-yl)-N-3-(4-methoxyphenoxy) propyl]aminomethyl]phenoxy]butyric acid or a salt thereof.

(44) The pharmaceutical composition for the prevention and/or treatment of metabolic syndrome according to any one of (41) to (43) above, wherein the statin is pitavastatin.

(45) A method for preventing and/or treating metabolic syndrome in a patient, the method including administering to the patient having metabolic syndrome an effective amount of a prophylactic and/or therapeutic agent for metabolic syndrome including the compound represented by the above formula (1) or a salt thereof, and a statin in combination.

(46) The method for preventing and/or treating metabolic syndrome in a patient according to (45) above, wherein the compound represented by the formula (1) is (R)-2-[3-[[N-(benzoxazol-2-yl)-N-3-(4-methoxyphenoxy) propyl]aminomethyl]phenoxy]butyric acid or a salt thereof.

(47) The method for preventing and/or treating metabolic syndrome in a patient according to (45) or (46) above, wherein the statin is pitavastatin.

(48) Use of the compound represented by the above formula (1) or a salt thereof, and a statin, for the manufacture of a pharmaceutical composition for the prevention and/or treatment of metabolic syndrome.

(49) The use according to (48) above, wherein the compound represented by the formula (1) is (R)-2-[3-[[N-(benzoxazol-2-yl)-N-3-(4-methoxyphenoxy) propyl]aminomethyl]phenoxy]butyric acid or a salt thereof.

(50) The use according to (48) or (49) above, wherein the statin is pitavastatin.

(51) A compound represented by the above formula (1) or a salt thereof for the prevention and/or treatment of metabolic syndrome, used in combination with a statin.

(52) The compound or salt for the prevention and/or treatment according to (51) above, wherein the compound represented by the formula (1) is (R)-2-[3-[[N-(benzoxazol-2-yl)-N-3-(4-methoxyphenoxy)propyl]aminomethyl]phenoxy] butyric acid or a salt thereof.

(53) The compound or salt for the prevention and/or treatment according to (51) or (52) above, wherein the statin is pitavastatin.

Effects of the Invention

The prophylactic and/or therapeutic agent for hyperlipidemia of the present invention has an excellent effect of lowering the cholesterol concentration and the triglyceride concentration in blood plasma by combining two drugs, and is also effective in the treatment or prevention of abnormal lipid metabolism such as familial hyperlipidemia which shows resistance to the treatments with existing drugs. Furthermore, the prophylactic and/or therapeutic agent is also effective in the prevention and/or treatment of obesity or diabetes mellitus, and in the prevention and/or treatment of metabolic syndrome.

BEST MODE FOR CARRYING OUT THE INVENTION

Figure 1:
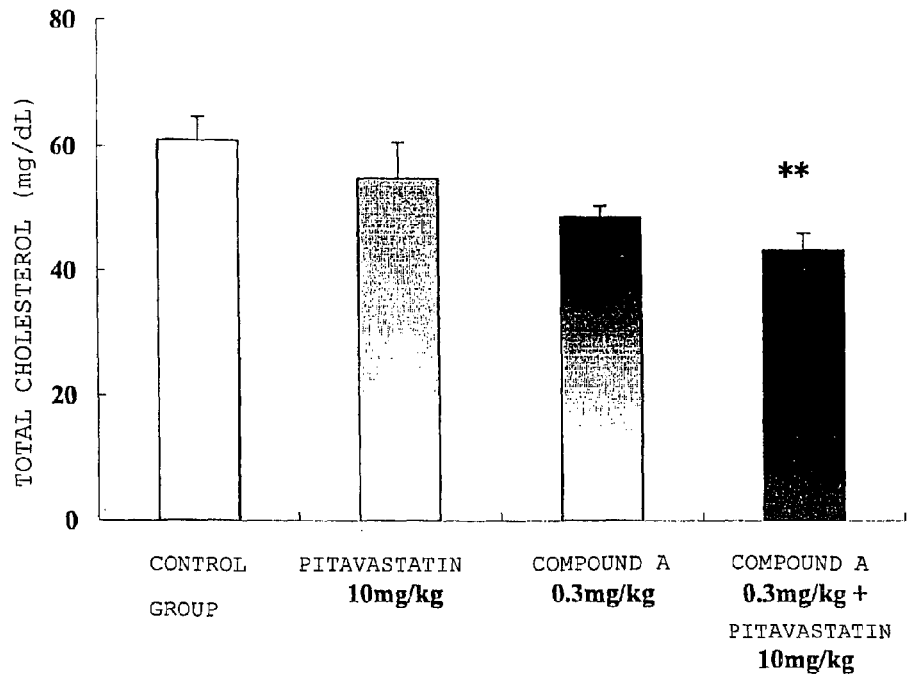
FIG. 1 shows the effects of the medicament on the total cholesterol concentration in blood plasma.

The statin according to the present invention includes a medicament (statin) having an effect of inhibiting HMG-CoA (3-hydroxy-3-methylglutaryl coenzyme A) reductase, which is a rate controlling enzyme for cholesterol biosynthesis, and for example, simvastatin (U.S. Pat. No. 4,444,784), pravastatin (U.S. Pat. No. 4,346,227), cerivastatin (U.S. Pat. No. 5,177,080), pitavastatin (U.S. Pat. No. 5,856,336, JP-A No. 1-279866) and the like. A preferred statin includes pitavastatin.

The pitavastatin used for the present invention includes pitavastatin or a salt thereof, or lactone derivatives of the compound and the salt, and also includes hydrates, and solvates with a pharmaceutically acceptable solvent, of the compound and the salt. Pitavastatin has a cholesterol synthesis inhibitory effect based on HMG-CoA reductase inhibition, and is known as a therapeutic drug for hyperlipidemia. The salt of pitavastatin includes an alkali metal salt such as a sodium salt or a potassium salt; an alkaline earth metal salt such as a calcium salt or a magnesium salt; an organic amine salt such as a phenethylamine salt; an ammonium salt; or the like. Among these, as the pitavastatin, a salt of pitavastatin is preferred, and in particular, a calcium salt and a sodium salt are preferred.

Pitavastatin can be produced by the methods described in U.S. Pat. No. 5,856,336 and JP-A No. 1-279866.

The phenoxybutyric acid derivative represented by the above-described formula (1) or a salt thereof used in the present invention can be produced by the method described in International Patent Application Publication No. WO 2005/023777 pamphlet. With regard to the formula (1), the halogen atom includes a chlorine atom, a bromine atom, an iodine atom or the like; the alkyl group includes a straight-chained or branched alkyl group having 1 to 4 carbon atoms, such as a methyl group or an ethyl group; and the alkoxy group includes a straight-chained or branched alkoxy group having 1 to 4 carbon atoms, such as a methoxy group or an ethoxy group. Furthermore, the alkyl group having 1 to 4 carbon atoms in the alkylcarbonyloxy group having 1 to 4 carbon atoms, the di-(alkyl having 1 to 4 carbon atoms) amino group, the alkylsulfonyloxy group having 1 to 4 carbon atoms, the alkylsulfonyl group having 1 to 4 carbon atoms, the alkylsulfinyl group having 1 to 4 carbon atoms, the alkylthio group having 1 to 4 carbon atoms, and the alkyloxycarbonyl group having 1 to 4 carbon atoms includes the above-mentioned alkyl group. In the case where $R^3a$ and $R^3b$, or $R^4a$ and $R^4b$ are joined and together represent an alkylenedioxy group includes an alkylenedioxy group in which an oxygen atom is bound to both ends of a straight-chained or branched alkylene group having 1 to 6, preferably 1 to 3, carbon atoms. Also, n and m are integers which are the numbers indicating the length of a methylene group.

In the formula (1), a preferred $R^1$ group includes an alkyl group having 1 to 4, preferably 2 to 4, carbon atoms; a preferred $R^2$ group includes a hydrogen atom; a preferred $R^3a$ group and a preferred $R^3b$ group includes a hydrogen atom; a preferred $R^4a$ group includes an alkoxy group having 1 to 4, preferably 1 to 2, carbon atoms; and a preferred $R^4b$ group includes a hydrogen atom. Further, a preferred X group includes an oxygen atom; a preferred Y group includes an oxygen atom; and a preferred Z group includes CH, that is, resulting in a benzene ring. Among these, 2-[3-[[N-(benzoxazole-2-yl)-N-3-(4-methoxyphenoxy)propyl]aminomethyl]phenoxy]butyric acid, or a salt thereof is preferred, and (R)-2-[3-[[N-(benzoxazole-2-yl)-N-3-(4-methoxyphenoxy)propyl]aminomethyl]phenoxy]butyric acid is particularly preferred.

The present invention is to administer a combination of a statin and a phenoxybutyric acid derivative represented by the above formula (1) or a salt thereof, and as shown in the following Examples, when pitavastatin is used as the statin, and this is used in combination with the phenoxybutyric acid derivative represented by the formula (1) or a salt thereof in rats, the combination has a strong effect of lowering the total cholesterol concentration, the LDL-cholesterol concentration and the triglyceride concentration in the blood plasma, as compared with the case of administering each of them individually. In particular, the combination offers a remarkable effect of strongly lowering the total cholesterol concentration and LDL-cholesterol concentration in blood plasma. Furthermore, a combined use of the two drugs has an excellent effect in a patient not exhibiting a marked response to single administration of statin. Therefore, the prophylactic and/or therapeutic agent for hyperlipidemia of the present invention is also effective in the treatment of hyperlipidemia, particularly in the treatment of type IIb and type IV hyperlipidemia showing high levels in both the cholesterol concentration and triglyceride concentration in blood plasma, as well as in the treatment of abnormal lipid metabolism such as familial hyperlipidemia showing resistance to a treatment with existing drugs. Furthermore, in Zucker fatty rats which are animals having a notably high plasma triglyceride concentration, and showing hypercholesterolemia, high blood glucose level, hyperinsulinemia and obesity, combined administration of pitavastatin and the phenoxybutyric acid derivative represented by the formula (1) or a salt thereof results in a pronounced plasma triglyceride concentration lowering effect, compared to individual administration of each drug, and thus the usefulness of the prophylactic and/or therapeutic agent for hyperlipidemia of the present invention is supported by the observation. Also, in Zucker fatty rat, combined administration of pitavastatin and the phenoxybutyric acid derivative represented by the formula (1) or a salt thereof results in an inhibitory effect on the increase in blood glucose level, and thus the prophylactic and/or therapeutic agent for diabetes mellitus of the present invention is also effective in the treatment of diabetes mellitus.

Moreover, combined administration of pitavastatin and the phenoxybutyric acid derivative represented by the formula (1) or a salt thereof is known to be effective in relation to excessive visceral fat, abnormal glucose metabolism and abnormal lipid metabolism which are considered as risk factors for metabolic syndrome. That is, the medicament provided by the present invention improves abnormal glucose metabolism, i.e., impaired glucose tolerance, and abnormal lipid metabolism, i.e., hypertriglyceridemia, in an animal model having excessively accumulated visceral obesity, such as in Zucker fatty rat, and thus the medicament can provide an excellent effect against metabolic syndrome.

In the medicament of the present invention, the dosage form of the statin and the phenoxybutyric acid derivative represented by the formula (1) or a salt thereof can be appropriately selected in accordance with the state of patient and the like, and include, e.g., any of powders, granules, dry syrups, tablets, capsules, injections and the like. These dosage forms can be produced by conventional production methods known to those ordinarily skilled in the art, by mixing a pharmaceutically acceptable carrier with the statin and the phenoxybutyric acid derivative represented by the formula (1) or a salt thereof. Furthermore, a preparation containing a statin, particularly pitavastatin, and a preparation including the phenoxybutyric acid derivative represented by the formula (1) or a salt thereof, can also be administered respectively.

In the case of preparing a solid preparation for oral administration as such a preparation, an excipient, and as necessary, a binding agent, a disintegrant, a gliding agent, a colorant, a savoring agent, a flavoring agent and the like are added to the ingredients, and then the resulting mixture can be produced into tablets, granules, powders, capsules or the like by a standard method. Such additives can be those generally used in the related art, for example, the excipient includes lactose, sodium chloride, glucose, starch, microcrystalline cellulose, silicic acid and the like; the binding agent includes water, ethanol, propanol, simple syrup, gelatin solution, hydroxypropylcellulose, methylcellulose, ethylcellulose, shellac, calcium phosphate, polyvinylpyrrolidone and the like; the disintegrant includes powdered agar, sodium hydrogen carbonate, sodium lauryl sulfate, stearic acid monoglyceride and the like; the gliding agent includes purified talc, stearic acid salts, borax, polyethylene glycol and the like; the colorant includes (β-carotene, yellow ferric oxide, caramel and the like; and the savoring agent includes sucrose, orange peel and the like.

In the case of preparing a liquid preparation for oral administration, an ingestive liquid preparation, a syrup, an elixir or the like can be produced according to a standard method by adding a savoring agent, a buffering agent, a stabilizing agent, a preservative and the like. Such additives can be those generally used in the related art, for example, the savoring agent includes sucrose and the like; the buffering agent includes sodium citrate and the like; the stabilizing agent includes tragacanth and the like; and the preservative includes paraoxybenzoic acid ester and the like.

In the case of preparing an injectable preparation, a subcutaneous injection, intramuscular injection and an intravenous injection can be produced according to a standard method by adding a pH adjusting agent, a stabilizing agent, and an isotonic agent. Such additives can be those generally used in the related art, for example, the pH adjusting agent includes sodium phosphate and the like; the stabilizing agent includes sodium pyrosulfite and the like; and the isotonic agent includes sodium chloride.

The usage form of the medicament of the present invention is not particularly limited, as long as the dosage form can provide synergistic preventive and/or therapeutic effects against hyperlipidemia, obesity, diabetes mellitus or metabolic syndrome, by using a statin, particularly pitavastatin, and the phenoxybutyric acid derivative represented by the formula (1) or a salt thereof in combination, and administering both of the drugs. The statin, particularly pitavastatin, and the phenoxybutyric acid derivative represented by the formula (1) or a salt thereof may be administered simultaneously, or may also be administered separately at an interval. That is, the statin, particularly pitavastatin, and the phenoxybutyric acid derivative represented by the formula (1) or a salt thereof may be prepared into a single preparation, or the two drugs may also be prepared into separate preparations and used as a set (kit).

In the present invention, when the two drugs are administered as a single preparation, it is preferable that the mixing ratio of the statin, particularly pitavastatin, and the phenoxybutyric acid derivative represented by the formula (1) or a salt thereof is, for example, in the range of 1:3 to 2000:1, and more preferably in the range of 1:2 to 100:1, by mass, in the case where the statin is pitavastatin, from the viewpoint that a particularly excellent synergistic effect can be obtained.

Furthermore, in the present invention, when the two drugs are prepared into separate preparations, the preparation containing statin, particularly pitavastatin, is provided as a prophylactic and/or therapeutic agent for hyperlipidemia, obesity, diabetes mellitus or metabolic syndrome that is administered in combination with a phenoxybutyric acid derivative represented by the formula (1) or a salt thereof, and on the other hand, the preparation containing the phenoxybutyric acid derivative represented by the formula (1) or a salt thereof is provided as a prophylactic and/or therapeutic agent for hyperlipidemia, obesity, diabetes mellitus or metabolic syndrome that is administered in combination with a statin, particularly pitavastatin. The formulation of the two drugs can be the same, or can be different. Also, the frequency of administration of each of the components can be different.

Furthermore, in the present invention, the amount of administration for the two drugs would be sufficient if they are effective amounts, and are appropriately selected on the basis of the symptoms. However, for example, when pitavastatin is used as the statin, pitavastatin can be administered in an amount of 0.01 to 50 mg, preferably 0.1 to 20 mg, and more preferably 1 to 10 mg, per day, and the phenoxybutyric acid derivative represented by the formula (1) or a salt thereof may be administered in an amount of 0.0001 to 1000 mg, and preferably 0.001 to 100 mg, per day. The administration can be carried out once or more than twice a day The present invention is illustrated in more detail by the following examples, but should not be construed to be limited thereto.

EXAMPLE 1

The effect of administering (R)-2-[3-[[N-(Benzoxazol-2-yl)-N-3-(4-methoxyphenoxy)propyl]aminomethyl]phenoxy]butyric acid (hereinafter, indicated as compound A) and pitavastatin calcium hydrate (containing 10.5% by mass of water; hereinafter, indicated as pitavastatin) on the total plasma cholesterol concentration and the like, was determined according to the following methods.

1. Test Animal and Breeding Environment

Male Sprague Dawley rats (Crl: CD (SD), Japan Charles River Co. Ltd., 6 weeks old) were taken for the test.

Throughout the test period, the rats were bred in a breeding room maintained with a light/dark cycle (bright period under room light: 7 A.M. to 7 P.M.) at a temperature of 23±3° C. and a humidity of 55±15%, and were allowed to freely take solid feedstuff (CE-2; Oriental Yeast Co. Ltd.) and tap water.

2. Preparation of Drugs

Compound A and pitavastatin were each suspended in a 0.5 mass % aqueous solution of methylcellulose (Metolose (registered trademark) SM-400, Shin-Etsu Chemical Co. Ltd.), and the amount of administration of the aqueous solution was adjusted to be 2 mL/kg. The suspension was stored in a shading bottle under refrigeration (4° C.), and the preparation was performed once every 7 days. Additionally, when the pitavastatin is a hydrate as in the case of the present Example, the water content of a standard product can be measured by a conventional method known to those ordinarily skilled in the art, and the amount required in the production of drug based on the water content of the "pitavastatin calcium hydrate" used in the present Example can be calculated.

3. Testing Method

In order to average the total cholesterol concentration and the triglyceride concentration in blood plasma, the rats were divided into the following four groups (eight animals each group), that is, a control group as a first group, a group administered with pitavastatin only (10 mg/kg) as a second group, a group administered with compound A only (0.3 mg/kg) as a third group, and a group administered with pitavastatin (10 mg/kg) and compound A (0.3 mg/kg) in combination as a fourth group.

The two medicaments were orally administered repeatedly for 14 days at a rate of once a day (in the morning). The control group of the first group was orally administered with 2 mL/kg of a 0.5 mass % aqueous solution of methylcellulose.

On the 7$^{th}$ day and the 14$^{th}$ day after the initiation of administration, the rats were fasted for 4 hours from administration, then blood was collected, and the total cholesterol concentration and triglyceride concentration in blood plasma were measured by enzymatic methods. Furthermore, the LDL-cholesterol concentration in blood plasma was measured using high performance liquid chromatography according to the method of Usui et al. (Lipid Res., 43:805-814, 2002).

4. Statistical Analysis and Data Processing Method

The results were shown in the form of average value±standard error. A multiple group comparison between the control group and the drug administered groups was conducted using Dunnett's multiple comparison test. A risk rate of less than 5% was determined to have a significant difference.

5. Test Results

The total cholesterol concentration in blood plasma after one week from administration is shown in FIG. 1 and Table 1. The ordinate axis in FIG. 1 indicates the total cholesterol concentration (mg/dL), and the abscissa axis shows, from the left, the control group of the first group, the group administered with pitavastatin only (10 mg/kg) of the second group, the group administered with compound A only (0.3 mg/kg) of the third group, and the group administered with pitavastatin (10 mg/kg) and compound A (0.3 mg/kg) in combination of the fourth group. The symbol ** in FIG. 1 indicates that there is a significant difference of p<0.01.

TABLE 1

Synergistic effect of combined use of medicaments on total cholesterol concentration in blood plasma

| Group name | Average value ± Standard error | Relative value compared to control group |
| --- | --- | --- |
| (1) Control group | 61.0 ± 3.8 | 1.000 |
| (2) Pitavastatin 10 mg/kg | 55.1 ± 5.7 | 0.903 |
| (3) Compound A 0.3 mg/kg | 48.3 ± 1.8 | 0.792 |
| (4) Group of drugs (2) and (3) in combination | 43.5 ± 2.8** | 0.713 |

**p < 0.01.
N = 8.

As the results, the total cholesterol concentration in blood plasma merely indicated a tendency of decrease, in the group administered with compound A only and the group administered with pitavastatin only (the relative indices with respect to the control group were 0.903 and 0.792, respectively). On the contrary, the group administered with a combination of the two drugs indicated a considerable decrease in the total cholesterol concentration in blood plasma compared to the group administered with pitavastatin only, and also indicated an obvious total cholesterol concentration lowering effect with a risk rate of p<0.01 (see the symbol ** in Table 1) as compared with the control group. Furthermore, this result was examined using Bürgi's method, and the relative index of the group administered with combined drugs (0.713) was smaller than the product of the respective relative indices of the groups administered with single drug (0.715=0.903×0.792), and thus a synergistic effect resulting from the combined administration was observed.

The effect of administration of medicament combination on the LDL-cholesterol concentration in blood plasma one week after the administration was reviewed. The results are shown in the following Table 2.

TABLE 2

Synergistic effect of combined use of medicaments on LDL-cholesterol concentration in blood plasma

| Group name | Average value ± Standard error | Relative value compared to control group |
| --- | --- | --- |
| (1) Control group | 11.6 ± 1.1 | 1.000 |
| (2) Pitavastatin 10 mg/kg | 11.3 ± 1.8 | 0.974 |
| (3) Compound A 0.3 mg/kg | 8.1 ± 0.4** | 0.698 |
| (4) Group of drugs (2) and (3) in combination | 7.2 ± 0.4*** | 0.621 |

**p < 0.01,
***p < 0.001.
N = 8.

As the results, the group administered with pitavastatin only did not have any difference compared to the control group (0.974), and the statin-only administered group was not observed to have a lowering effect. However, the group administered with compound A only and the group administered with a combination of the two drugs were observed to have significant lowering effects (p<0.01 (see the symbol  in Table 2)). Furthermore, in the group administered with a combination of the two drugs, the LDL-cholesterol concentration in blood plasma was considerably decreased compared to the group administered with compound A only, and an obvious decrease in the LDL-cholesterol concentration in blood plasma with a risk rate of p<0.001 (see the symbol * in Table 2) was observed compared to the control group. This effect was reviewed using the above-mentioned Bürgi's method, and the relative index of the group administered with combined drugs (0.621) was smaller than the product of the respective relative indices of the groups administered with single drug (0.680=0.974×0.698), and thus a synergistic effect resulting from the combined administration was observed. Although this operating mechanism is not clear, the result that the medicament according to the present invention strongly lowered the total cholesterol concentration and LDL-cholesterol concentration in blood plasma in an animal model for a disease condition showing resistance to HMG-CoA reductase, should be noted.

Furthermore, the total cholesterol concentration and triglyceride concentration in blood plasma measured two weeks after the initiation of administration were also reviewed. The results are shown in the following Table 3.

TABLE 3

(2) Synergistic effect of combined use of drugs on the total cholesterol concentration in blood plasma

| Group name | Average value ± Standard error | Relative value compared to control group |
| --- | --- | --- |
| (1) Control group | 57.7 ± 2.6 | 1.000 |
| (2) Pitavastatin 10 mg/kg | 57.5 ± 6.6 | 0.997 |
| (3) Compound A 0.3 mg/kg | 43.4 ± 1.9* | 0.752 |
| (4) Group of drugs (2) and (3) in combination | 39.3 ± 2.3** | 0.681 |

*p < 0.05,
**p < 0.01,
N = 8.

As the results, no difference was observed between the group administered with pitavastatin only and the control group (0.997), and no effect was observed with the single administration of statin on the total cholesterol concentration in blood plasma. However, the group administered with compound A only and the group administered with the two drugs in combination were observed to have significant lowering effects (p<0.05 (see the symbol * in Table 3)). Furthermore, the group administered with the two drugs in combination indicated a decrease in the total cholesterol concentration in blood plasma to a large extent compared to the group administered with pitavastatin only, and also indicated an obvious effect of decreasing the total cholesterol concentration in blood plasma with a risk rate of p<0.01 (see the symbol ** in Table 3), compared to the control group. This effect was reviewed using the above-mentioned Bürgi's method, and the relative index of the group administered with combined drugs (0.681) was smaller than the product of the respective relative indices of the groups administered with single drug (0.750=0.997×0.752), and thus a synergistic effect resulting from the combined administration was observed.

A similar review was carried out on the triglyceride concentration in blood plasma. The results are shown in the following Table 4.

TABLE 4

Synergistic effect of combined use of drugs on the triglyceride concentration in blood plasma

| Group name | Average value ± Standard error | Relative value compared to control group |
| --- | --- | --- |
| (1) Control group | 41.3 ± 3.2 | 1.000 |
| (2) Pitavastatin 10 mg/kg | 38.9 ± 3.1 | 0.942 |
| (3) Compound A 0.3 mg/kg | 33.3 ± 2.2 | 0.806 |
| (4) Group of drugs (2) and (3) in combination | 30.4 ± 1.6* | 0.736 |

*p < 0.05.
N = 8.

As the results, the group administered with compound A only and the group administered with pitavastatin only, merely indicated a tendency of decrease (the relative indices with respect to the control group were 0.942 and 0.806, respectively). On the contrary, the group administered with the two drugs in combination indicated a considerable decrease in the triglyceride concentration in blood plasma compared to the group administered with pitavastatin only, and also indicated an obvious effect of decreasing the triglyceride concentration in blood plasma with a risk rate of p<0.05 (see the symbol * in Table 4), compared to the control group. This effect was reviewed using the above-mentioned Bürgi's method, and the relative index of the group administered with combined drugs (0.736) was smaller than the product of the respective relative indices of the groups administered with single drug (0.759=0.942×0.806), and thus a synergistic effect resulting from the combined administration was observed.

As indicated in the above data, synergistic effects of lowering the total cholesterol concentration, LDL-cholesterol concentration and triglyceride concentration in blood plasma, resulting from the administration of the two medicaments in combination, were confirmed. Also, it was confirmed that the medicament of the present invention has an extremely effective preventing and/or treating effect against the disease condition of showing resistance to the existing treatment with HMG-CoA reductase.

EXAMPLE 2

Zucker fatty rat is an animal having a notably high plasma triglyceride concentration, and also showing hypercholesterolemia, high blood glucose level, hyperinsulinemia and obesity, and is used as a model for pharmacological assessment of therapeutic agents for hyperlipidemia and anti-obestic drugs. With regard to the plasma triglyceride concentration in a Zucker fatty rat, statin showed a lowering effect of 20% to 26%, whereas clofibrate and fenofibrate did not show any lowering effect, has been reported (Atherosclerosis, 74, 15-21 (1988); Atherosclerosis, 29, 269-275 (1978)). Since fenofibrate is known to show a triglyceride concentration lowering effect in the animal model used in Example 1, the Zucker fatty rat can be an animal model indicating high resistance to therapeutic agents for hyperlipidemia. The effect of administration of compound A and pitavastatin on the plasma triglyceride concentration in this animal model was determined according to the following methods.

1. Test Animal and Breeding Environment

Male Zucker fatty rats (Crlj: ZUC-Lepr$^{fa}$, Japan Charles River Co. Ltd., 10 weeks old) were taken for the test.

Throughout the test period, the rats were bred in a breeding room maintained with a light/dark cycle (bright period under room light: 7 A.M. to 7 P.M.) at a temperature of 23±3° C. and a humidity of 55±15%, and were allowed to freely take solid feedstuff (CE-2; Oriental Yeast Co. Ltd.) and tap water.

2. Preparation Of Drugs

Compound A, pitavastatin and fenofibrate (Sigma-Aldrich Co. Ltd.) were each suspended in a 0.5 mass % aqueous solution of methylcellulose (Metolose (registered trademark) SM-400, Shin-Etsu Chemical Co. Ltd.), and the amount of administration of the aqueous solution was adjusted to be 2 mL/kg. The suspension was stored in a shading bottle under refrigeration (4° C.), and the preparation was carried out once every 7 days. Additionally, when the pitavastatin was a hydrate as in the case of the present Example, the water content of a standard product was measured by a conventional method known to those ordinarily skilled in the art, and the amount required in the production of drug based on the water content of the "pitavastatin calcium hydrate" used in the present Example was calculated.

3. Experimental Methods

In order to average the total cholesterol concentration and the triglyceride concentration in blood plasma, the rats were divided into the following six groups (eight animals each group), that is, a control group as a first group, a group administered with compound A only (0.1 mg/kg) as a second group, a group administered with pitavastatin only (10 mg/kg) as a third group, a group administered with fenofibrate only (100 mg/kg) as a fourth group, a group administered with pitavastatin (10 mg/kg) and compound A (0.1 mg/kg) in combination as a fifth group, and a group administered with pitavastatin (10 mg/kg) and fenofibrate (100 mg/kg) in combination as a sixth group.

The two medicaments were orally administered repeatedly for 14 days at a rate of once a day (in the morning). The control group of the first group was orally administered with 2 mL/kg of a 0.5 mass % aqueous solution of methylcellulose.

On the 14$^{th}$ day after the initiation of administration, the rats were fasted for 4 hours from administration, then blood was collected, and the triglyceride concentration in blood plasma was measured by an enzymatic method.

4. Statistical Analysis and Data Processing Method

The results were shown in the form of average value±standard error. A multiple group comparison between the control group and the drug administered groups was conducted using Dunnett's multiple comparison test. A risk rate of less than 5% was determined to have a significant difference.

5. Test Results

Figure 2:
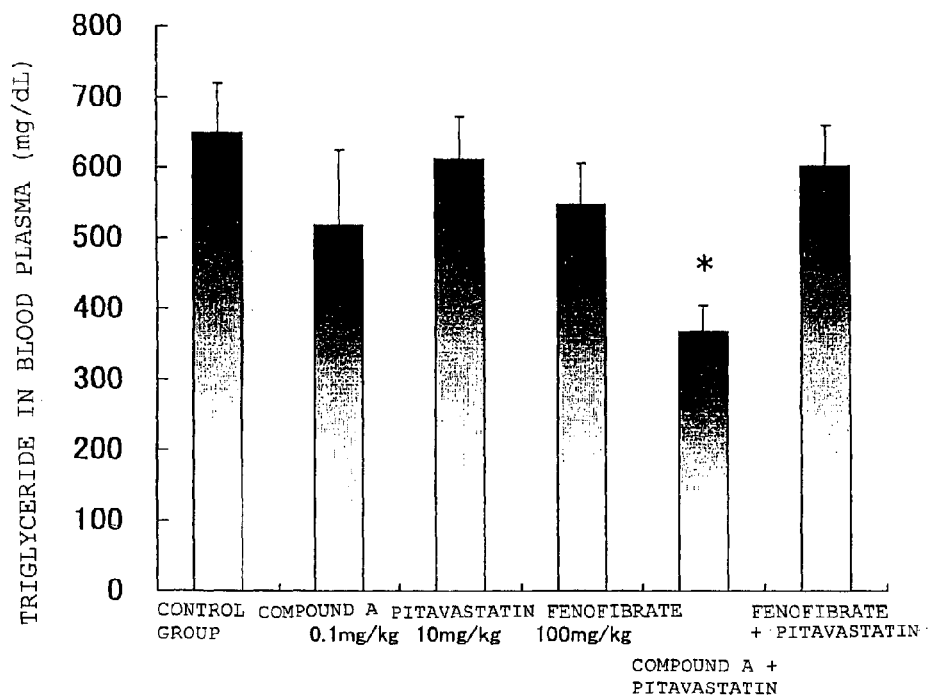
FIG. 2 shows the effects of the medicament on the triglyceride concentration in blood plasma.

Table 5 and FIG. 2 show the triglyceride concentration in blood plasma after two weeks from administration. The ordinate axis in FIG. 2 indicates the triglyceride concentration (mg/dL), and the abscissa axis shows, from the left, the control group of the first group, the group administered with compound A only (0.1 mg/kg) of the second group, the group administered with pitavastatin only (10 mg/kg) of the third group, the group administered with fenofibrate only (100 mg/kg) of the fourth group, the group administered with pitavastatin (10 mg/kg) and compound A (0.1 mg/kg) in combination of the fifth group, and the group administered with pitavastatin (10 mg/kg) and fenofibrate (100 mg/kg) in combination of the sixth group. The symbol * in FIG. 2 indicates that there is a significant difference of $p<0.05$.

TABLE 5

Synergistic effect of combined use of drugs on the triglyceride concentration in blood plasma

| Group name | Average value ± Standard error | Relative value compared to control group |
|---|---|---|
| (1) Control group | 649.3 ± 70.2 | 1.000 |
| (2) Compound A 0.1 mg/kg | 518.0 ± 106.0 | 0.798 |
| (3) Pitavastatin 10 mg/kg | 612.2 ± 61.0 | 0.943 |
| (4) Fenofibrate 100 mg/kg | 546.3 ± 58.9 | 0.841 |
| (5) Group of drugs (2) and (3) in combination | 367.7 ± 36.2 * | 0.566 |
| (6) Group of drugs (3) and (4) in combination | 602.2 ± 57.6 | 0.928 |

* $p < 0.05$.
N = 7-8.

With regard to the triglyceride concentration in blood plasma, almost equal rates of decrease were observed in the group administered with compound A only and the group administered with fenofibrate only (20% and 16%, respectively). The rate of decrease was 6% in the group administered with pitavastatin only. On the contrary, the group administered with compound A and pitavastatin in combination was observed to have a notable triglyceride lowering effect, and the rate of decrease was 43%, which was also statistically significant. When the presence or absence of any synergistic effect was measured using Bürgi's formula, the relative value of the groups administered with two drugs in combination with respect to the control group (0.566) was considerably lower compared to the product of the respective relative values for the groups administered with single drug (0.798× 0.943=0.753). Thus, it was shown that the effect observed this time was synergistic for the groups administered with drugs in combination. On the other hand, in the group administered with fenofibrate and pitavastatin in combination, such effect was not observed.

Accordingly, it was confirmed that the medicament of the present invention exhibits an extremely excellent lipid lowering effect in the cases where the existing inventions hardly indicate effects.

EXAMPLE 3

As also discussed in Example 2, since Zucker fatty rat shows high blood glucose level, the animal is used as an animal model for investigating the effect of medicaments for diabetes mellitus. As a method for examining diabetes mellitus, an oral glucose tolerance test, that is, a method in which a test subject fasted overnight is orally fed with a glucose solution, and blood is collected before and after the feeding, to examine the degree of increase in the blood glucose level, is widely performed. Thus, the Zucker fatty rat was used and administered with medicaments, and then an oral glucose tolerance test was performed to investigate the influence of the medicament of the present invention exerted on the blood glucose level.

1. Test Animal and Breeding Environment

Male Zucker fatty rats (Crlj: ZUC-Lepr$^{fa}$, Japan Charles River Co. Ltd., 9 weeks old) were taken for the test.

Throughout the test period, the rats were bred in a breeding room maintained with a light/dark cycle (bright period under room light: 7 A.M. to 7 P.M.) at a temperature of 23±3° C. and a humidity of 55±15%, and were allowed to freely take solid feedstuff (CE-2; Oriental Yeast Co. Ltd.) and tap water.

2. Preparation of Drugs

Compound A, pitavastatin and fenofibrate (Sigma-Aldrich Co. Ltd.) were each suspended in a 0.5 mass % aqueous solution of methylcellulose (Metolose (registered trademark) SM-400, Shin-Etsu Chemical Co. Ltd.), and the amount of administration of the aqueous solution was adjusted to be 2 mL/kg. The suspension was stored in a shading bottle under refrigeration (4° C.), and the preparation was carried out once every 7 days. Additionally, when the pitavastatin was a hydrate as in the case of the present Example, the water content of a standard product was measured by a conventional method known to those ordinarily skilled in the art, and the amount required in the production of drug based on the water content of the "pitavastatin calcium hydrate" used in the present Example was calculated.

3. Testing Method

In order to average the total cholesterol concentration and the triglyceride concentration in blood plasma, the rats were divided into the following six groups (eight animals each group), that is, a control group as a first group, a group administered with compound A only (0.3 mg/kg) as a second group, a group administered with pitavastatin only (3 mg/kg) as a third group, a group administered with fenofibrate only (100 mg/kg) as a fourth group, a group administered with pitavastatin (3 mg/kg) and compound A (0.1 mg/kg) in combination as a fifth group, and a group administered with pitavastatin (3 mg/kg) and fenofibrate (100 mg/kg) in combination as a sixth group.

The two medicaments were orally administered repeatedly for 28 days at a rate of once a day (in the morning). The control group of the first group was orally administered with 2 mL/kg of a 0.5 mass % aqueous solution of methylcellulose.

On the 28$^{th}$ day after the initiation of administration, the rats were fasted overnight and administered with drug, and after one hour, an oral glucose tolerance test was performed. The blood glucose level was measured by an enzymatic method.

4. Statistical Analysis and Data Processing Method

The results were shown in the form of average value±standard error. A multiple group comparison between the control group and the drug administered groups was conducted using Dunnett's multiple comparison tests. A risk rate of less than 5% was determined to have a significant difference.

5. Test Results

Figure 3:
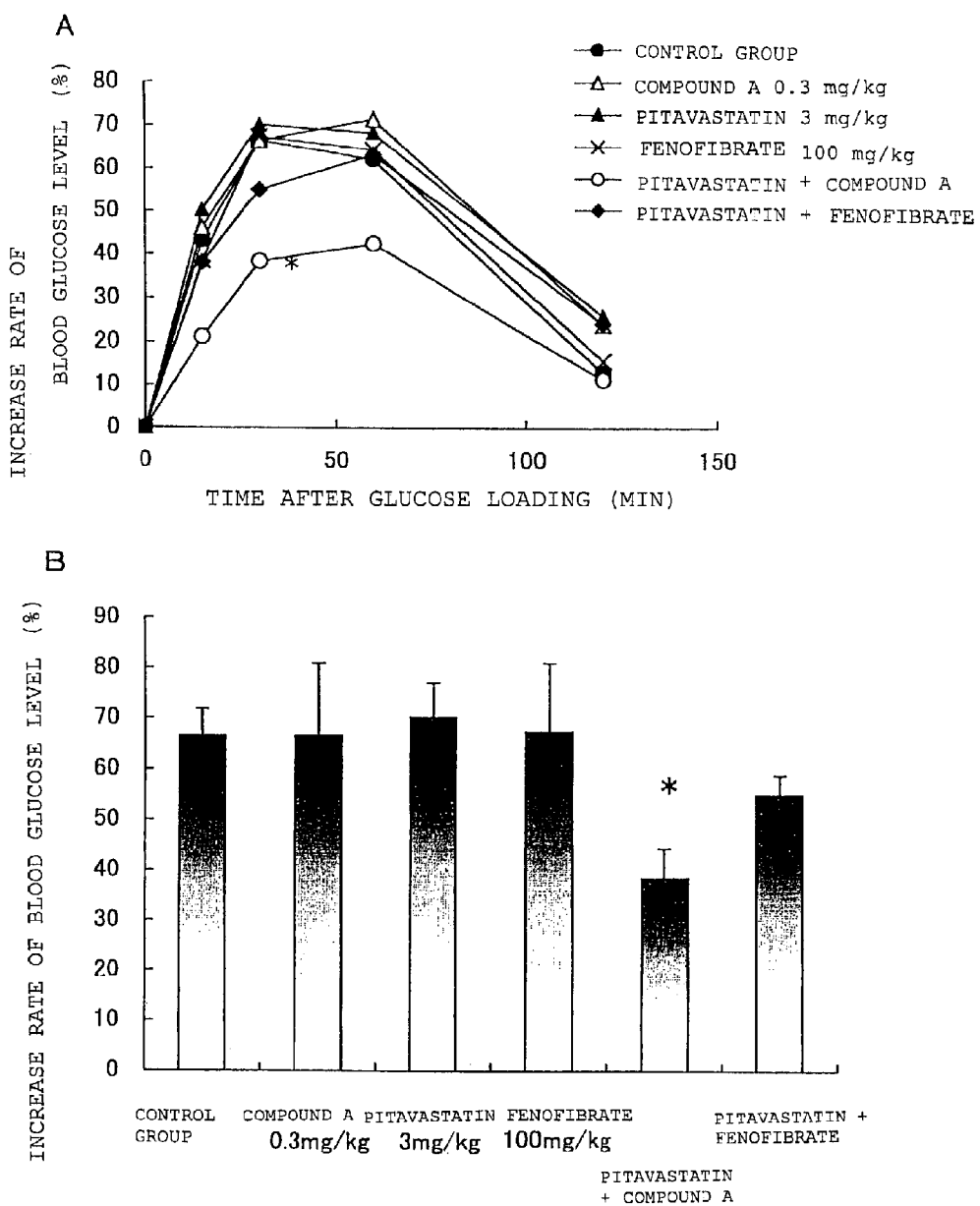
FIG. 3 shows the effects of the medicament on the increase in the blood glucose level in an oral glucose tolerance test.

FIG. 3A shows changes in the increase rate of blood glucose level over time in the oral glucose tolerance test, and FIG. 3B shows the amount of increase in the blood glucose level 30 minutes after glucose loading, where the blood glucose level in the control group is shown to be the maximum. The ordinate axis in FIG. 3A indicates the increase rate (%) of the blood glucose level, and the abscissa axis indicates the time (minutes) from the glucose loading. The ordinate axis in FIG. 3B indicates the increase rate (%) of the blood glucose level, and the abscissa axis show, from the left, the control group of the first group, the group administered with compound A only (0.3 mg/kg) of the second group, the group administered with pitavastatin only (3 mg/kg) of the third group, the group administered with fenofibrate only (100 mg/kg) of the fourth group, the group administered with pitavastatin (3 mg/kg) and compound A (0.3 mg/kg) in combination of the fifth group, and the group administered with pitavastatin (3 mg/kg) and fenofibrate (100 mg/kg) in combination of the sixth group. The symbol * in FIG. 3A and FIG. 3B indicates that there is a significant difference of $p<0.05$.

The blood glucose level on an empty stomach in the control group on the day of performing the oral glucose tolerance test was 153.0±4.6 mg/dL. Additionally, there was no difference between the drug administered groups. As shown in FIG. 3A, when glucose was loaded, the control group, the group administered with compound A only, the group administered with pitavastatin only, the group administered with fenofibrate only, and the group administered with pitavastatin and fenofibrate in combination showed rapid increases in the blood glucose level. On the contrary, in the group administered with pitavastatin and compound A in combination, increase in the blood glucose level was clearly suppressed. As shown in FIG. 3B, when the increase rate of the blood glucose level obtained 30 minutes after the glucose loading where the blood glucose level of the control group reached the maximum, none of the groups administered with single drug were observed to have differences with the control group, but the group administered with pitavastatin and compound A in combination clearly suppressed an increase in the blood glucose level. Additionally, at this time point, the group administered with pitavastatin and fenofibrate in combination suppressed an increase in the blood glucose level only slightly.

Therefore, it was proved that the medicament created by the present invention exhibits an extremely excellent effect also on diabetes mellitus.

Furthermore, with regard to the risk factor of metabolic syndrome, excessive visceral fat, abnormal glucose metabolism, abnormal lipid metabolism and hypertension, when the results of Example 2 and Example 3 are taken together and contemplated, it is suggested that the medicament is effective to the foregoing three terms. That is, in an animal model such as Zucker fatty rat, in which visceral obesity has excessively accumulated, the medicament provided by the present invention improved abnormal glucose metabolism, i.e., abnormal glucose tolerance, and abnormal lipid metabolism, i.e., hypertriglyceridemia, and therefore, the medicament is expected to have an excellent effect against metabolic syndrome.

INDUSTRIAL APPLICABILITY

The present invention is to provide a medicament having an effect of strongly decreasing the total cholesterol concentration, LDL-cholesterol concentration, triglyceride concentration and blood glucose level, and in particular, strongly lowering the LDL-cholesterol concentration. In particular, the medicament of the present invention is to provide a medicament very effective against a disease condition wherein single administration of a statin does not exhibit obvious effects, and the medicament is useful in the pharmaceutical industries, and has industrial applicability.

The invention claimed is:

1. A therapeutic agent for hyperlipidemia, comprising:
a compound represented by the following formula (1):

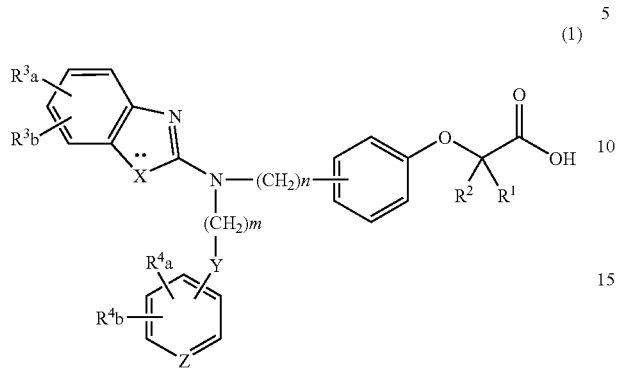

wherein $R^1$ and $R^2$, which may be identical or different, each represent a hydrogen atom, a methyl group or an ethyl group; $R^3a$, $R^3b$, $R^4a$ and $R^4b$, which may be identical or different, each represent a hydrogen atom, a halogen atom, a nitro group, a hydroxyl group, a $C_{1-4}$ alkyl group, a trifluoromethyl group, a $C_{1-4}$ alkoxy group, a $C_{1-4}$ alkylcarbonyloxy group, a di-$C_{1-4}$ alkylamino group, a $C_{1-4}$ alkylsulfonyloxy group, a $C_{1-4}$ alkylsulfonyl group, a $C_{1-4}$ alkylsulfinyl group, or a $C_{1-4}$ alkylthio group, or $R^3a$ and $R^3b$, or $R^4a$ and $R^4b$ are joined to represent an alkylenedioxy group; X represents an oxygen atom, a sulfur atom or N-$R^5$ wherein $R^5$ represents a hydrogen atom, a $C_{1-4}$ alkyl group, a $C_{1-4}$ alkylsulfonyl group, or a $C_{1-4}$ alkyloxycarbonyl group; Y represents an oxygen atom, a S(O)1 group wherein 1 represents a number from 0 to 2, a carbonyl group, a carbonylamino group, an aminocarbonyl group, a sulfonylamino group, an aminosulfonyl group, or an NH group; Z represents CH or N; n represents a number from 1 to 6; and m represents a number from 2 to 6, or a salt of said compound; and a pitavastatin, or a salt thereof, or a lactone thereof, or a hydrate thereof or a hydrate of a salt thereof in combination, wherein the compound represented by the formula (1) is (R)-2-[3-[[N-(benzoxazol-2-yl)-N-3-(4-methoxyphenoxy)propyl]aminomethyl]phenoxy]butyric acid or a salt thereof.

2. The therapeutic agent according to claim 1, wherein the hyperlipidemia is familial hyperlipidemia.

3. A therapeutic agent for diabetes mellitus, comprising:
a compound represented by the following formula (1):

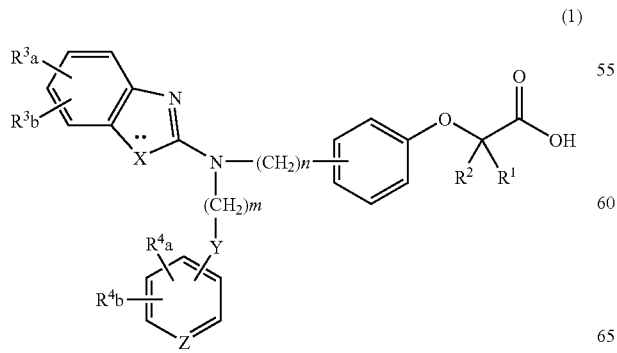

wherein $R^1$ and $R^2$, which may be identical or different, each represent a hydrogen atom, a methyl group or an ethyl group; $R^3a$, $R^3b$, $R^4a$ and $R^4b$, which may be identical or different, each represent a hydrogen atom, a halogen atom, a nitro group, a hydroxyl group, a $C_{1-4}$ alkyl group, a trifluoromethyl group, a $C_{1-4}$ alkoxy group, a $C_{1-4}$ alkylcarbonyloxy group, a di-$C_{1-4}$ alkylamino group, a $C_{1-4}$ alkylsulfonyloxy group, a $C_{1-4}$ alkylsulfonyl group, a $C_{1-4}$ alkylsulfinyl group, or a $C_{1-4}$ alkylthio group, or $R^3a$ and $R^3b$, or $R^4a$ and $R^4b$ are joined to represent an alkylenedioxy group; X represents an oxygen atom, a sulfur atom or N-$R^5$ wherein $R^5$ represents a hydrogen atom, a $C_{1-4}$ alkyl group, a $C_{1-4}$ alkylsulfonyl group, or a $C_{1-4}$ alkyloxycarbonyl group; Y represents an oxygen atom, a S(O)1 group wherein 1 repressents a number from 0 to 2, a carbonyl group, a carbonylamino group, an aminocarbonyl group, a sulfonylamino group, an aminosulfonyl group, or an NH group; Z represents CR or N; n represents a number from 1 to 6; and m represents a number from 2 to 6, or a salt of said compound; and a pitavastatin, or a salt thereof, or a lactone thereof, or a hydrate thereof or a hydrate of a salt thereof in combination, wherein the compound represented by the formula (1) is (R)-2-[3-[[N-(benzoxazol-2-yl)-N-3-(4-methoxyphenoxy)propyl]aminomethyl]phenoxy]butyric acid or a salt thereof.

4. A therapeutic agent for metabolic syndrome, comprising:
a compound represented by the following formula (1):

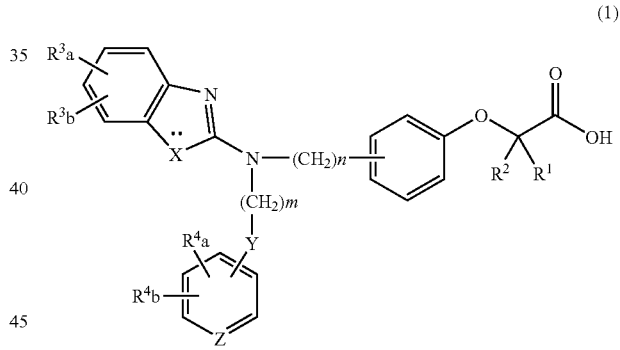

wherein $R^1$ and $R^2$, which may be identical or different, each represent a hydrogen atom, a methyl group or an ethyl group; $R^3a$, $R^3b$, $R^4a$ and $R^4b$, which may be identical or different, each represent a hydrogen atom, a halogen atom, a nitro group, a hydroxyl group, a $C_{1-4}$ alkyl group, a trifluoromethyl group, a $C_{1-4}$ alkoxy group, a $C_{1-4}$ alkylcarbonyloxy group, a di-$C_{1-4}$ alkylamino group, a $C_{1-4}$ alkylsulfonyloxy group, a $C_{1-4}$ alkylsulfonyl group, a $C_{1-4}$ alkylsulfinyl group, or a $C_{1-4}$ alkylthio group, or $R^3a$ and $R^3b$, or $R^4a$ and $R^4b$ are joined to represent an alkylenedioxy group; X represents an oxygen atom, a sulfur atom or N-$R^5$ wherein $R^5$ represents a hydrogen atom, a $C_{1-4}$ alkyl group, a $C_{1-4}$ alkylsulfonyl group, or a $C_{1-4}$ alkyloxycarbonyl group; Y represents an oxygen atom, a S(O)1 group wherein 1 represents a number from 0 to 2), a carbonyl group, a carbonylarnino group, an aminocarbonyl group, a sulfonylamino group, an aminosulfonyl group, or an NH group; Z represents CH or N; n represents a number from 1 to 6; and m represents a number from 2 to 6, or a salt of said compound; and a pitavastatin, or a salt thereof, or a lactone thereof, or a hydrate thereof or a hydrate of a salt thereof in combination, wherein the compound represented by the formula (1) is (R)-2-[3-[[N-(benzoxazol-2-yl)-N-3-(4-methoxyphenoxy)propyl]aminomethyl]phenoxy]butyric acid or a salt thereof.

* * * * *